United States Patent [19]

Strack et al.

[11] Patent Number: 5,482,772

[45] Date of Patent: Jan. 9, 1996

[54] POLYMERIC STRANDS INCLUDING A PROPYLENE POLYMER COMPOSITION AND NONWOVEN FABRIC AND ARTICLES MADE THEREWITH

[75] Inventors: David C. Strack, Canton; Tracy N. Wilson, Woodstock; Donald V. Willitts, Fairburn, all of Ga.

[73] Assignee: Kimberly-Clark Corporation, Neenah, Wis.

[21] Appl. No.: 997,406

[22] Filed: Dec. 28, 1992

[51] Int. Cl.[6] .................................................. B32B 49/00
[52] U.S. Cl. ........................ 428/357; 428/374; 428/296; 428/364; 428/369; 428/370; 428/373
[58] Field of Search .................................. 428/357, 474.1, 428/476.1, 516, 412, 355, 349, 475.8, 475.5, 364, 365, 372, 373, 374; 525/221, 222, 240; 156/308.2, 327; 604/393, 394, 385.1, 383

[56] References Cited

U.S. PATENT DOCUMENTS

| | | | |
|---|---|---|---|
| 3,595,731 | 7/1971 | Davies et al. | 161/150 |
| 4,041,203 | 8/1977 | Brock et al. | 428/157 |
| 4,068,036 | 1/1978 | Stanistreet | 428/296 |
| 4,211,819 | 7/1980 | Kunimune et al. | 428/374 |
| 4,523,336 | 6/1985 | Truman | 2/69 |
| 4,551,378 | 11/1985 | Carey, Jr. | 428/198 |
| 4,691,081 | 9/1987 | Gupta et al. | 174/105 R |
| 4,741,941 | 5/1988 | Englebert et al. | 428/71 |
| 4,759,986 | 7/1988 | Hwo | 428/349 |
| 4,770,656 | 9/1988 | Proximine et al. | 604/393 |
| 4,808,176 | 2/1989 | Kielpikowski | 604/385.2 |
| 4,808,662 | 2/1989 | Hwo | 525/74 |
| 4,834,738 | 5/1989 | Kielpikowski | 604/385.2 |
| 4,842,596 | 6/1989 | Kielpikowski | 604/385.2 |
| 5,057,361 | 10/1991 | Sayovitz et al. | 428/290 |
| 5,346,756 | 9/1994 | Ogale et al. | 428/288 |

FOREIGN PATENT DOCUMENTS

| | | | |
|---|---|---|---|
| 9409193 | 4/1994 | WIPO . | |
| WO95/04182 | 2/1995 | WIPO | D04H 13/00 |

Primary Examiner—Patrick J. Ryan
Assistant Examiner—Merrick Dixon
Attorney, Agent, or Firm—Michael U. Lee

[57] ABSTRACT

Single and multicomponent polymeric strands including a blend of a melt-extrudable polyolefin and a heterophasic polypropylene composition. The heterophasic polypropylene composition includes three polymers and is normally not melt-spinable into strands by itself. In the multicomponent strands, the blend is in one side or the sheath. Fabric made with such strands is also disclosed and has improved combinations of strength, abrasion resistance, and softness properties. Composite materials including the foregoing fabric bonded to both sides of an inner meltblown layer are also disclosed. In addition, garments made with the fabric are disclosed.

16 Claims, 5 Drawing Sheets

POLYMERIC STRANDS INCLUDING A PROPYLENE POLYMER COMPOSITION AND NONWOVEN FABRIC AND ARTICLES MADE THEREWITH

TECHNICAL FIELD

This invention generally relates to polymeric fibers and filaments and products such as nonwoven fabrics made with polymeric fibers and filaments. More particularly, this invention relates to single component and multicomponent polymeric fibers and filaments which include propylene polymer compositions, and nonwoven fabrics and garments made with such fibers and filaments.

BACKGROUND OF THE INVENTION

Polymeric fibers and filaments are used to make a variety of products including yarns, carpets, woven fabrics, and nonwoven fabrics. As used herein, polymeric fibers and filaments are referred to generically as polymeric strands. Filaments mean continuous strands of material and fibers mean cut or discontinuous strands having a definite length.

It is often desirable that polymeric strands and articles made with polymeric strands be soft and strong. This is particularly true for nonwoven fabric and articles made with nonwoven fabric. Nonwoven fabrics are typically used to make garments such as work wear, medical apparel, and absorbent articles. Absorbent products made with nonwoven fabric include infant care items such as diapers, child care items such as training pants, feminine care items such as sanitary napkins, and adult care items such as incontinence products.

Nonwoven fabrics are commonly made by meltspinning thermoplastic materials. Meltspun fabrics are called spunbond materials and methods for making spunbond materials are well-known. U.S. Pat. No. 4,692,618 to Dorschner et al. and U.S. Pat. No. 4,340,563 to Appel et al. both disclose methods for making spunbond nonwoven webs from thermoplastic materials by extruding the thermoplastic material through a spinneret and drawing the extruded material into filaments with a stream of high velocity air to form a random web on a collecting surface. For example, U.S. Pat. No. 3,692,618 to Dorschner et al. discloses a process wherein bundles of polymeric filaments are drawn with a plurality of eductive guns by very high speed air. U.S. Pat. No. 4,340,563 to Appel et al. discloses a process wherein thermoplastic filaments are drawn through a single wide nozzle by a stream of high velocity air. The following patents also disclose typical meltspinning processes: U.S. Pat. No. 3,338,992 to Kinney; U.S. Pat. No. 3,341,394 to Kinney; U.S. Pat. No. 3,502,538 to Levy; U.S. Pat. No. 3,502,763 to Hartmann; U.S. Pat. No. 3,909,009 to Hartmann; U.S. Pat. No. 3,542,615 to Dobo et al.; and Canadian Patent Number 803,714 to Harmon.

Spunbond materials with desirable combinations of physical properties, especially combinations of strength, durability, and softness have been produced, but limitations have been encountered. For example, in some applications, polymeric materials such as polypropylene may have a desirable level of strength but not a desirable level of softness. On the other hand, materials such as polyethylene may, in some cases, have a desirable level of softness but a not a desirable level of strength.

In an effort to produce nonwoven materials having desirable combinations of physical properties, nonwoven fabrics comprising multicomponent strands such as bicomponent strands or multiconstituent strands such as biconstituent strands have been developed.

Methods for making bicomponent nonwoven materials are well-known and are disclosed in patents such as Reissue 30,955 of U.S. Pat. No. 4,068,036 to Stanistreet, U.S. Pat. No. 3,423,266 to Davies et al., and U.S. Pat. No. 3,595,731 to Davies et al. A bicomponent nonwoven fabric is made from polymeric fibers or filaments including first and second polymeric components which remain distinct. The first and second components of multicomponent strands are arranged in substantially distinct zones across the cross-section of the strands and extend continuously along the length of the strands. Typically, one component exhibits different properties than the other so that the strands exhibit properties of the two components. For example, one component may be polypropylene which is relatively strong and the other component may be polyethylene which is relatively soft. The end result is a strong yet soft nonwoven fabric.

Multiconstituent strands are similar to multicomponent strands except that one component does not extend continuously along the length of the strands. The noncontinuous component is typically present as a multitude of discrete polymer segments connected by the other polymeric component.

Although conventional bicomponent and biconstituent nonwoven fabrics have desirable levels of strength, durability, and softness, there is still a need for nonwoven materials which are made with polymeric strands and have particular combinations of strength, durability, and softness. Furthermore, there is a need for garments made with nonwoven materials having particular combinations of strength, durability, and softness.

SUMMARY OF THE INVENTION

Accordingly, an object of the present invention is to provide improved polymeric strands and products made therewith such as nonwovens and garments.

Another object of the present invention is to provide polymeric strands, nonwoven fabrics made with polymeric strands, and articles such as garments made with nonwoven fabrics, each having desirable levels of strength, durability, and softness.

A further object of the present invention is to provide soft yet strong and durable garments such as medical apparel, workwear, and absorbent articles.

Thus, the present invention provides a polymeric strand including a first polymeric component comprising a blend of:

(a) a melt-extrudable polyolefin; and (b) a polypropylene composition comprising:

(i) a first polymer which is a propylene polymer comprising 85% by weight of propylene and having an isotactic index greater than 85;

(ii) a second polymer which is a polymer comprising ethylene and being insoluble in xylene at about 23° C.; and (iii) a third polymer which is an amorphous copolymer of ethylene and propylene, the amorphous copolymer being soluble in xylene at about 23° C.

The polypropylene composition is preferably present in the first polymeric component in an amount up to about 40% by weight. In addition, the first polymer is preferably present in the polypropylene composition in an amount from about 10 to about 60 parts by weight, the second polymer is preferably present in the polypropylene composition in an amount from about 10 to about 40 parts by weight, and the third polymer is preferably present in the polypropylene composition in an amount from about 30 to about 60 parts by weight. Still more particularly, the third polymer preferably includes ethylene in an amount from about 40 to about 70% by weight. The polypropylene composition, by itself, is heterophasic and normally not melt-spinable into strands, and particularly not into spunbond strands.

Suitable melt-extrudable polyolefins for the first polymeric component include crystalline polyolefins, and more particularly, include polypropylene, random copolymers of propylene and ethylene, and poly(4-methyl-1-pentene).

According to another aspect of the present invention, the polymeric strand is a multicomponent strand and further includes a second melt-extrudable polymeric component. The first and second components of the multicomponent strand are arranged in substantially distinct zones across the cross-section of the multicomponent strand and extend continuously along the length of the multicomponent strand. The first component of the multicomponent strand constitutes at least a portion of the peripheral surface of the strand continuously along the length of the strand.

More particularly, the second component of the multicomponent strand includes a crystalline polyolefin. Suitable polyolefins for the second component of the multicomponent strand include polypropylene, random copolymers of propylene and ethylene and poly(4-methyl-1-pentene). Suitable configurations for the first and second components of the multicomponent strand include a side-by-side configuration and a sheath/core configuration.

The present invention also comprehends a nonwoven fabric made with the above described polymeric strands and further comprehends garment materials made with such nonwoven fabric. The addition of the heterophasic polypropylene composition enhances the strength of the polymeric strands and the nonwoven fabric and garments made therewith while maintaining, and sometimes enhancing, acceptable levels of durability and softness.

Still further objects and the broad scope of the applicability of the present invention will become apparent to those of skill in the art from the details given hereafter. However, it should be understood that the detailed description of the preferred embodiments of the present invention is only given by way of illustration because various changes and modifications well within the spirit and scope of the invention should become apparent to those of skill in the art in view of the following detailed description.

DETAILED DESCRIPTION OF THE INVENTION

Figure 1:
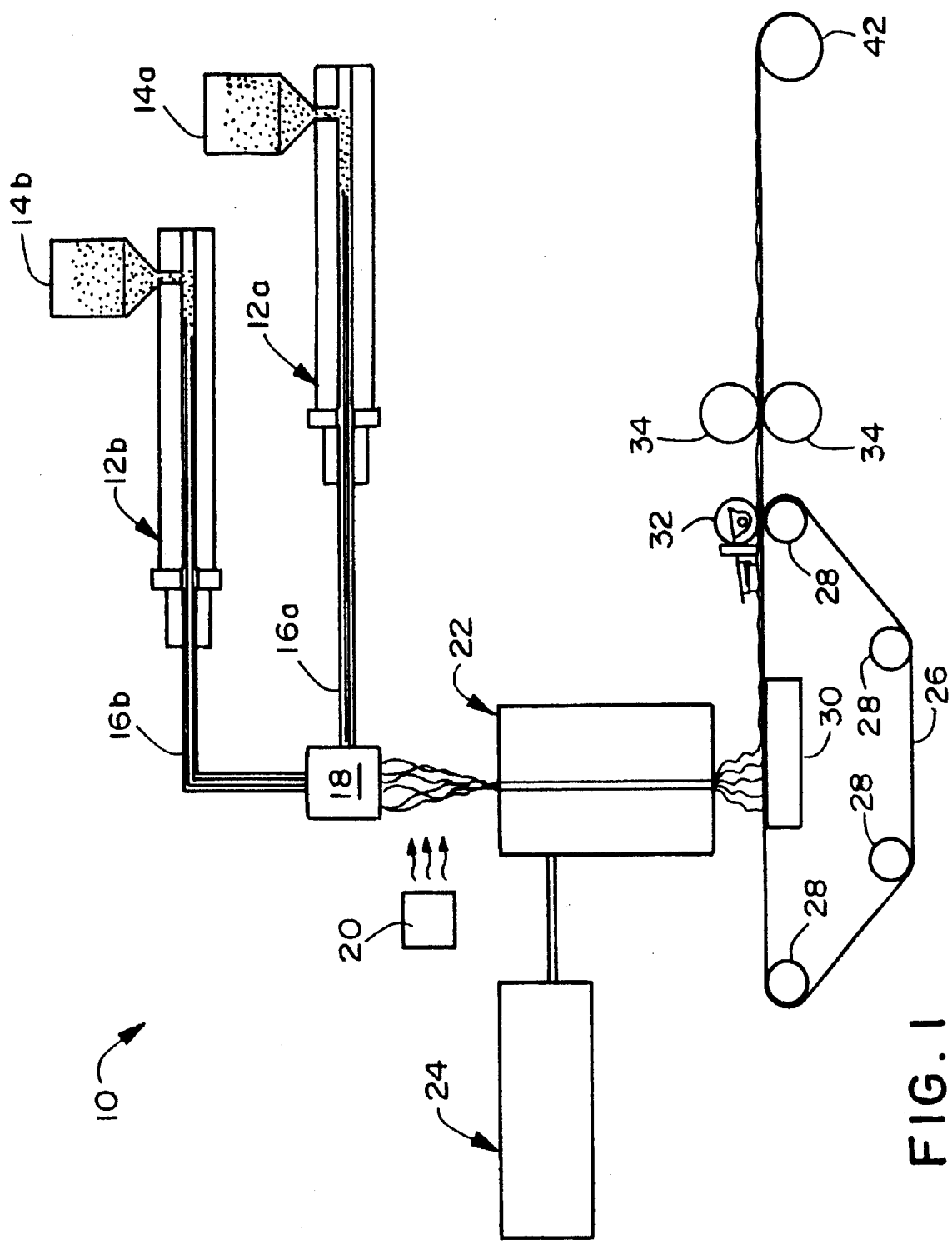
FIG. 1 is a schematic drawing of a process line for making a preferred embodiment of the present invention.

As discussed above, the present invention provides polymeric strands useful for making articles such as nonwoven fabrics. Nonwoven fabrics made with the polymeric strands of the present invention are strong and durable, yet soft. The nonwoven fabrics of the present invention can be used to make other useful articles.

Generally described, the polymeric strand of the present invention includes a first polymeric component comprising a blend of: (a) a melt-extrudable polyolefin; and (b) a polypropylene composition comprising:
 (i) a first polymer which is a propylene polymer comprising 85% by weight of propylene and having an isotactic index greater than 85;
 (ii) a second polymer which is a polymer comprising ethylene and being insoluble in xylene at about 23° C.; and
 (iii) a third polymer which is an amorphous copolymer of ethylene and propylene, the amorphous copolymer being soluble in xylene at about 23° C.

The term "strands" as used herein refers to an elongated extrudate formed by passing a polymer through a forming orifice such as a die. Strands include fibers, which are discontinuous strands having a definite length, and filaments, which are continuous strands of material. The polymeric strands of the present invention can be single component, multicomponent, or multiconstituent polymeric strands although bicomponent polymeric strands are preferred. Single component polymeric strands of the present invention are preferably made only with the above-described blend. Multicomponent strands, however, further include a second melt-extrudable polymeric component. The first and second components of the multicomponent strand are arranged in substantially distinct zones across the cross-section of the multicomponent strand and extend continuously along the length of the multicomponent strand. The first component of the multicomponent strand constitutes at least a portion of the peripheral surface of the strand continuously along the length of the strand. The multicomponent strands are particularly suited for making loftier, through-air bonded nonwovens.

As used herein, the terms "nonwoven web" and "nonwoven fabric" are used interchangeable to mean a web of material which is formed without the use of weaving processes. Weaving processes produce a structure of individual strands which are interwoven and identifiable repeating manner. Nonwoven webs may be formed by a variety of processes such as meltblowing, spunbonding, film aperturing, and staple fiber carding. The nonwoven fabric of the present invention may be formed from staple single component or multicomponent fibers or both. Such staple fibers may be carded and bonded to form the nonwoven fabric. Preferably, however, the nonwoven fabric of the present invention is made with continuous spunbond multicomponent filaments which are extruded, drawn, and laid on a traveling forming surface. A preferred process for making the nonwoven fabrics of the present invention is disclosed in detail below.

The nonwoven fabrics of the present invention can be used to make garments such as workwear, medical apparel and wrapping material, and absorbent articles. Absorbent articles which can be made with the nonwoven fabric of the present invention include infant care items such as diapers, child care items such as training pants, feminine care items such as sanitary napkins and adult care items such as incontinence products. The nonwoven fabric of the present invention can also be used to make absorbent products such as wipes.

Suitable melt-extrudable polymers for the first component of the polymeric strands include crystalline polyolefins, and more particularly, include polypropylene, random copolymers of propylene and ethylene, and poly(4-methyl-1-pentene). The melt-extrudable polyolefin should be compatible with the polypropylene composition which makes up the remainder of the first component so that a uniform and stable blend of the melt extrudable polyolefin and the polypropylene composition is achieved.

Suitable polypropylene compositions for the first component of the polymeric strands include polypropylene compositions such as that disclosed in European Patent Application Publication No. 0,400,333, the disclosure of which is incorporated herein by reference. European Patent Application Publication Number 0,400,333 is owned by Himont Inc. of New Castle County, Del. Such polypropylene compositions are known as heterophasic polypropylene compositions or catalloys. Catalloy stands for "catalyst-alloy, of various monomers or structures polymerized together." More specifically, the polypropylene composition of the first component of the polymeric strands of the present invention are, before blending with the melt-extrudable polyolefin, in the form of spheroidal particles with an average diameter between 500 and 7000 um. In addition, the first polymer is preferably present in the polypropylene composition in an amount from about 10 to about 60 parts by weight, the second polymer is preferably present in the polypropylene composition in an amount of from about 10 to about 40 parts by weight, and the third polymer is preferably present in the polypropylene composition in an amount from about 30 to about 60 parts by weight. Still more particularly, the third polymer preferably includes ethylene in an amount of from about 40 to about 70% by weight. A suitable commercially available polypropylene composition for the polymeric strands is KS-057P catalloy polymer available from Himont Inc.

As described in the above-referenced European publications, the heterophasic polypropylene compositions used to make the polymeric strands of the present invention are prepared through sequential polymerization in two or more stages, using highly stereo specific Ziegler-Natta catalysts. The first polymer, which is a propylene polymer comprising 85% by weight of propylene and having an isotactic index greater than 85, is formed during the first stage of polymerization, preferably in liquid monomer. The second and third polymers are formed during the subsequent polymerization stages in the presence of the first polymer formed in the first stage.

The sequential polymerization stages can be performed in an autoclave, the gas phase being continuously analyzed with a processing gas chromatograph. In the first stage, liquid polypropylene and a catalyst, described in more detail below, are introduced into the autoclave at 20° C. The temperature is brought to between 50° and 80° C. in about 10 minutes and the pressure is brought to about 30 atmospheres. That temperature and pressure are maintained for 20–30 minutes. Then, essentially all of the unreacted monomers are eliminated by way of degassing at 60° C. and atmospheric pressure. The polymerization of the first polymer may be done in the presence of ethylene or an alpha-olefin such as butene-1, pentene-1, 4-methylpentene-1, in such quantities that the isotactic index of the resulting process is greater than 85%.

The polypropylene from the first stage is then brought to a temperature between 50° and 70° C. and a pressure of 5–30 atmospheres by feeding, in order, propylene and ethylene at the ratio and in the quantity desired for achieving the desired composition. The temperature and pressure are maintained for 30 minutes–8 hours. Known traditional transfer agents such as hydrogen and $ZnEt_2$ can be used as molecular weight regulators. Copolymerization can also occur in the presence of another alpha-olefin or a diene, conjugated or not, such as butadiene, 1-4,hexadiene, 1,5-hexadiene and ethylidenenorbornene-1.

At the end of polymerization, the particulate polymer is discharged and stabilized and dried in an oven under nitrogen current at 60° C. More detailed process parameters are disclosed in European Patent Application Publication No. 0 400 333.

The catalyst used in the foregoing reaction includes the reaction products of:

1. A solid compound containing (a) a titanium compound, and (b) an electron donor compound (internal donor) supported on magnesium chloride; and 2. Al-trialkyl compound and an electron donor compound (external donor).

The catalyst typically has the following properties: (a) a surface area less than 100 meter square per gram, and preferably between 50 and 80 meter square per gram; (b) a porosity between 0.25 and 0.4 cc per gram; (c) a pore volume distribution such that more than 50% of the pores have a radius greater than 100 A.; and (d) and an x-ray spectrum presenting a halo with maximum intensity at 2 $\theta$ angles from 33.5° and 35° and where there is no reflection at 2 $\theta$ equals 14.95°.

A suitable titanium compound for the catalyst is titanium chloride and suitable internal electron donors for addition to the magnesium chloride include alkyl, cycloalkyl, or aryl phthalates such as diisobutyl, di-n-butyl, and di-n-octylphthalate.

Suitable Al-trialkyl compounds include Al-triethyl and Al-triisobutyl. Suitable external electron donor compounds include xylene compounds of the formula $R'R''Si(OR)_2$ where R' and R", equal or different, are alkyl, cycloalkyl or aryl radicals containing 1–18 carbon atoms, and R is a 1–4 carbon alkyl radical. Typical xylenes are diphenyldimethoxysilane, dicyclohexyldimethoxysilane, methyl-tert-butyldimethoxysilane, diisopropyldimethoxysilane, and phenyltriethoxysilane.

The catalyst is made by the following procedure:

A molten adduct of magnesium chloride and an alcohol such as C2H5OH, is emulsified in an inert hydrocarbon liquid immiscible with the adduct, and then cooling the emulsion very quickly in order to cause a solidification of the adduct in the form of a spheroidal particles containing three moles of alcohol per mole of magnesium chloride. The spheroidal particles are dealcoholized by heating the particles to between 50°–130° C. to reduce the alcohol content from 3 to 1–1.5 moles per mole of magnesium chloride. The adduct is suspended in titanium chloride cold, in a concentration of 40–50 grams per liter and brought to 80°–135° C. where the mixture is maintained for 1–2 hours. The internal electron donor compound is then added to the titanium chloride. The excess titanium chloride is separated while hot through filtration or sedimentation. The treatment with titanium chloride is then repeated one or two more times. The resulting solid is washed with hepatane or hexane and dried.

The solid titanium containing compound is then mixed with an Al-trialkyl compound and the external electron donor compound. The Al/Ti ratio is between 10 and 200 and the xylene/Al moler ratio is between 1/5 and 1/50. The catalyst may be then precontacted with small quantities of olefin which is then polymerized. Further details on production of the catalyst are disclosed in European Patent Application Publication No. 0 400 333.

When the polymer strand of the present invention is a multi-component strand, a suitable second component polymer includes melt-extrudable crystal and polyolefins. Particularly preferred second component polymers include polyolefins such as polypropylene, random copolymers of propylene and ethylene, and poly(4-methyl-1-pentene). A particularly suitable polymer for the second component is 3495 polypropylene available from Exxon Chemical of Houston, Tex.

The first component of the polymeric strands of the present invention preferably include the heterophasic polypropylene composition in an amount up to about 40% by weight of the first polymeric component. More preferably, the heterophasic polypropylene composition is present in the first polymeric component in an amount from about 5 to about 30% by weight. The remainder of the first component is preferably the melt-extrudable polyolefin.

When the polymeric strand of the present invention is a multi-component strand, the strand is preferably in a bicomponent configuration with either a sheeth/core arrangement or a side-by-side arrangement. The weight ratio of the first polymeric component to the second polymeric component may vary from 20/80 to 80/20, but preferably is about 50/50.

Figure 2A:
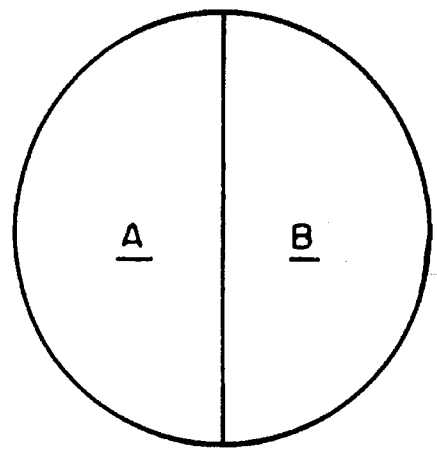
FIG. 2A is a schematic drawing illustrating the cross-section of a filament made according to a preferred embodiment of the present invention with the polymer components A and B in a side-by-side arrangement.
Figure 2B:
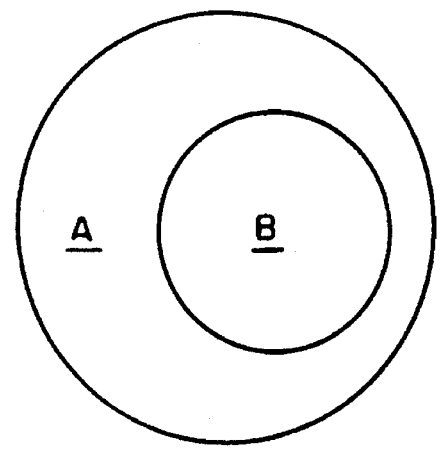
FIG. 2B is a schematic drawing illustrating the cross-section of a filament made according to a preferred embodiment of the present invention with the polymeric components A and B in an eccentric sheath/core arrangement.
Figure 2C:
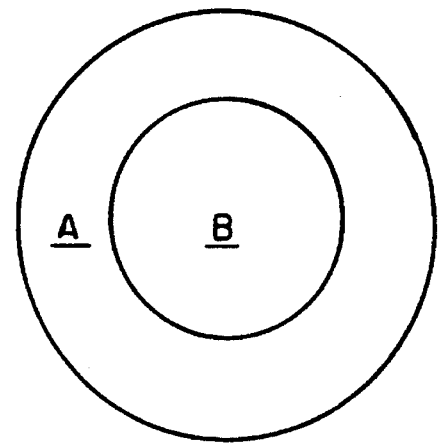
FIG. 2C is a schematic drawing illustrating the cross-section of a filament made according to a preferred embodiment of the present invention with the polymeric components A and B in a concentric sheath/core arrangement.

A preferred embodiment of the present invention is a bicomponent polymeric strand comprising a first polymeric component A and a second polymeric component B. The first and second components A and B may be arranged in a side-by-side arrangement as shown in FIG. 2A, and eccentric sheeth/core arrangement as shown in FIG. 2B, or a concentric sheeth/core arrangement as shown in FIG. 2C. Polymer component A is the sheet of the strand and polymer component B is the core of the strand in the sheet/core arrangement. When arranged in the side-by-side arrangement or the eccentric sheeth/core arrangement, the resulting strands tend to exhibit natural helical crimp. Methods for extruding bicomponent polymeric strands into such arrangements are well known to those of ordinary skill in the art. Although the embodiments disclosed herein include bicomponent filaments, it should be understood that the strands of the present invention may have more than two components.

A preferred combination of polymers for a bicomponent strand of the present invention is a blend of a random copolymer of propylene and ethylene, with 3% by weight ethylene, and a heterophasic polypropylene composition. The second component is preferably polypropylene. While the principal components of the polymeric strands of the present invention have been described above, such polymeric components can also include other material which do not adversely affect the objectives of the present invention. For example, the first and second polymeric components A and B can also include, without limitation, pigments, antioxidants, stabilizers, surfactants, waxes, float promoters, solid solvents, particulates and materials added to enhance processability of the composition.

Turning to FIG. 1, a process line 10 for preparing a preferred embodiment of the present invention is disclosed. The process line 10 is arranged to produce bicomponent continuous filaments, but it should be understood that the present invention comprehends nonwoven fabrics made with multicomponent filaments having more than two components. For example, the fabric of the present invention can be made with filaments having three or four components. It should be further understood that fabric of the present invention can also be made with single component filaments.

The process line 10 includes a pair of extruders 12a and 12b for separately extruding a polymer component A and a polymer component B. Polymer component A is fed into the respective extruder 12a from a first hopper 14a and polymer component B is fed into the respective extruder 12b from a second hopper 14b. Polymer components A and B are fed from the extruders 12a and 12b through respective polymer conduits 16a and 16b to a spinneret 18. Spinnerets for extruding bicomponent filaments are well-known to those of ordinary skill in the art and thus are not described here in detail. Generally described, the spinneret 18 includes a housing containing a spin pack which includes a plurality of plates stacked one on top of the other with a pattern of openings arranged to create flow paths for directing polymer components A and B separately through the spinneret. The spinneret 18 has openings arranged in one or more rows. The spinneret openings form a downwardly extending curtain of filaments when the polymers are extruded through the spinneret. Preferably, spinneret 18 is arranged to form side-by-side or eccentric sheath/core bicomponent filaments. Such configurations are shown in FIG. 2A and 2B respectively. The spinneret may also be arranged to form concentric sheath/core filaments as shown in FIG. 2C.

The process line 10 also includes a quench blower 20 positioned adjacent the curtain of filaments extending from the spinneret 18. Air from the quench air blower 20 quenches the filaments extending from the spinneret 18. The quench air can be directed from one side of the filament curtain as shown in FIG. 1, or both sides of the filament curtain.

A fiber draw unit or aspirator 22 is positioned below the spinneret 18 and receives the quenched filaments. Fiber draw units or aspirators for use in melt spinning polymers are well-known as discussed above. For example, suitable fiber draw units for use in the process of the present invention include a linear fiber aspirator of the type shown in U.S. Pat. No. 3,802,817, eductive guns of the type shown in U.S. Pat. Nos. 3,692,618 and 3,423,266, and a linear draw system such as that shown in U.S. Pat. No. 4,340,563, the disclosures of which patents are hereby incorporated herein by reference.

Generally described, the fiber draw unit 22 includes an elongated vertical passage through which the filaments are drawn by aspirating air entering from the sides of the passage and flowing downwardly through the passage. The aspirating air draws the filaments and ambient air through the fiber draw unit. The aspirating air can be heated by a heater 24 when a high degree of natural helical crimp in the filaments is desired.

An endless foraminous forming surface 26 is positioned below the fiber draw unit 22 and receives the continuous filaments from the outlet opening of the fiber draw unit. The forming surface 26 travels around guide rollers 28. A vacuum 30 positioned below the forming surface 26 where the filaments are deposited draws the filaments against the forming surface.

The process line 10 further includes a compression roller 32 which can be heated. The compression roller 32 along with the forward most of the guide rollers 28, receive the web as the web is drawn off of the forming surface 26. In addition, the process line includes a pair of thermal point bonding rollers 34 for bonding the bicomponent filaments together and integrating the web to form a finished fabric. Lastly, the process line 10 includes a winding roll 42 for taking up the finished fabric.

To operate the process line 10, the hopper 14a and 14b are filled with the respective polymer components A and B. Polymer components A and B are melted and extruded by the respected extruders 12a and 12b through polymer conduits 16a and 16b and the spinneret 18. Although the temperatures of the molten polymers vary depending on the polymers used, when random copolymer of ethylene and propylene and polypropylene are used as components A and B respectively, the preferred temperatures of the polymers range from about 370° to about 530° F. and preferably range from 390° to about 450° F.

As the extruded filaments extend below the spinneret 18, a stream of air from the quench blower 20 at least partially quenches the filaments. The partial quenching may be used to develop a latent helical crimp in the filaments. The quench air preferably flows in a direction substantially perpendicular to the length of the filaments at a temperature of about 45° to about 90° F. and a velocity from about 100 to about 400 feet per minute.

After quenching, the filaments are drawn into the vertical passage of the fiber draw unit 22 by a flow of air through the fiber draw unit. The fiber draw unit is preferably positioned 30 to 60 inches below the bottom of the spinneret 18. When filaments having minimal natural helical crimp are desired, the aspirating air is at ambient temperature. When filaments having a high degree of crimp are desired, heated air from the heater 24 is supplied to the fiber draw unit 22. For high crimp, the temperature of the air supplied from the heater 24 is sufficient that, after some cooling due to mixing with cooler ambient air aspirated with the filaments, the air heats the filaments to a temperature required to activate the latent crimp. The temperature required to activate the latent crimp of the filaments ranges from about 110° F. to a maximum temperature less than the melting point of the second component B. The temperature of the air from the heater 24 and thus the temperature to which the filaments are heated can be varied to achieve different levels of crimp. It should be further understood that the temperature of the air contacting the filaments to achieve the desired crimp will depend on factors such as the type of polymers in the filaments and the denier of the filaments.

Generally, a higher air temperature produces a higher number of crimps. The degree of crimp of the filaments may be controlled by controlling the temperature of the mixed air in the fiber draw unit 22 contacting the filaments. This allows one to change the resulting density, pore size distribution and drape of the fabric by simply adjusting the temperature of the air in the fiber draw unit.

Figure 3:
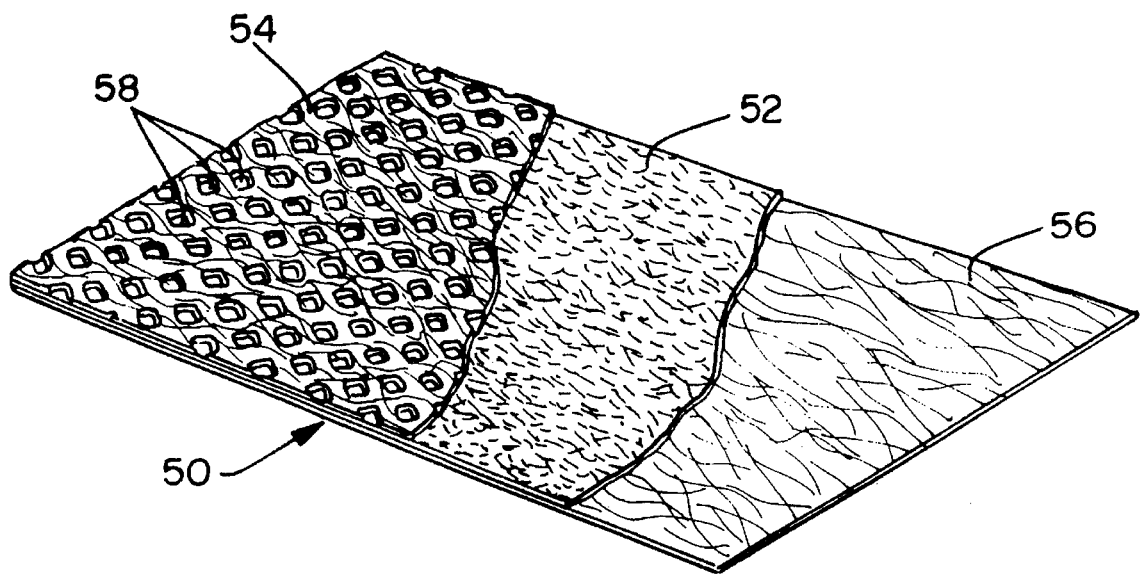
FIG. 3 is a fragmentary perspective view, with sections thereof broken away, of a point-bonded sample of multilayer fabric made according to a preferred embodiment of the present invention.
Figure 4:
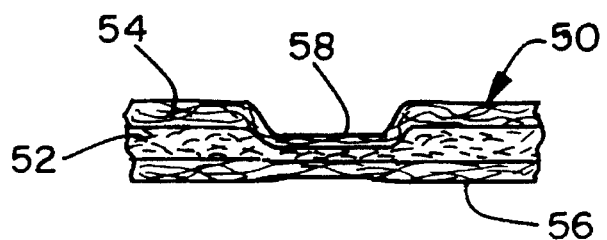
FIG. 4 is a cross-sectional view of the multilayer fabric of FIG. 3.

The drawn filaments are deposited through the outer opening of the fiber draw unit 22 onto the traveling forming surface 26. The vacuum 30 draws the filaments against the forming surface 26 to form an unbonded, nonwoven web of continuous filaments. The web is then lightly compressed by the compression roller 32 and thermal point bonded by bonding rollers 34. Thermal point bonding techniques are well known to those skilled in the art and are not discussed here in detail. Thermal point bonding in accordance with U.S. Pat. No. 3,855,046 is preferred and such reference is incorporated herein by reference. The type of bond pattern may vary based on the degree of strength desired. The bonding temperature also may vary depending on factors such as the polymers in the filaments but is preferably between about 240° and 255° F. As explained below, thermal point bonding is preferred when making cloth-like materials for garments such as medical apparel, work wear, and the outer cover of absorbent personal care items like baby diapers. A thermal point bonded material is shown in FIGS. 3 and 4. Lastly, the finished web is wound onto the winding roller 42 and is ready for further treatment or use.

When used to make liquid handling layers of liquid absorbent articles, the fabric of the present invention may be treated with conventional surface treatments or contain conventional polymer additives to enhance the wettability of the fabric. For example, the fabric of the present invention may be treated with polyalkalene-oxide modified siloxane and silanes such as polyalkaline-dioxide modified polydimethyl-siloxane as disclosed in U.S. Pat. No. 5,057,361. Such a surface treatment enhances the wettability of the fabric so that the nonwoven fabric is suitable as a liner or surge management material for feminine care, infant care, child care, and adult incontinence products. The fabric of the present invention may also be treated with other treatments such as antistatic agents, alcohol repellents, and the like, as known to those skilled in the art.

The resulting material is strong, yet durable and soft.. The addition of the heterophasic polypropylene composition which, by itself is normally not melt-spinable into strands, tends to enhance the strength of the fabric while maintaining, and sometimes improving, the softness and durability of the fabric.

When used as a garment material, the nonwoven fabric of the present invention preferably has a denier from about 1 to about 12 dpf and more preferably has a denier from about 2 to about 3.5 dpf. The lower denier imparts improved cloth-like tactile properties to the fabric. The basis weight of such materials may vary but preferably ranges from about 0.4 to about 3.0 osy.

Although the method of bonding shown in FIG. 1 is thermal point bonding, it should be understood that the fabric of the present invention may be bonded by other means such as oven bonding, ultrasonic bonding, hydroentangling or combinations thereof to make cloth-like fabric. Such bonding techniques are well known to those of ordinary skill in the art and are not discussed here in detail. If a loftier material is desired, a fabric of the present invention may be bonded by non-compressive means such as through-air bonding. Methods of through-air bonding are well known to those of skill in the art. Generally described, the fabric of the present invention may be through-air bonded by forcing air having a temperature above the melting temperature of the first component A of the filaments through the fabric as the fabric passes over a perforated roller. The hot air melts the lower melting polymer component A and thereby forms bonds between the bicomponent filaments to integrate the web. Such a high loft material is useful as a fluid management layer of personal care absorbent articles such as liner or surge materials in a baby diaper.

According to another aspect of the present invention, the above described nonwoven fabric may be laminated to one or more polymeric layers to form a composite material. For example, an outer cover material may be formed by laminating the spunbond, nonwoven, thermal point bonded fabric described above to a polymeric film. The polymeric film can act as a liquid barrier and preferably comprises a polyolefin such as polypropylene or polyethylene and preferably has a thickness less than about 1 mil. Low density polyethylene and relatively soft polypropylene are particularly preferred. The polymeric film can also be a coextruded film including, for example, an adhesive polymer such as ethylene methyl acrylate copolymer in the layer adjacent the nonwoven material and a polyolefin such as low density polyethylene or polypropylene in the outer layer. The adhesive layer preferably is about 20% by weight of the coextruded film and the outer layer preferably is about 80% by weight of the coextruded film.

According to another embodiment of the present invention, a first web of extruded multicomponent polymeric strands made as described above is bonded to a second web of extruded polymeric strands, the first and second webs being positioned in laminar surface-to-surface relationship. The second web may be a spunbond material, but for applications such as garment material for medical apparel or for sterile medical wrap, the second layer can be made by well known meltblowing techniques. The meltblown layer can act as a liquid barrier. Such laminates can be made in accordance with U.S. Pat. No. 4,041,203, the disclosure of which is incorporated herein by reference. U.S. Pat. No. 4,041,203 references the following publications on meltblowing techniques which are also incorporated herein by reference: An article entitled "Superfine Thermoplastic Fibers" appearing in INDUSTRIAL & ENGINEERING CHEMISTRY, Vol. 48, No. 8, pp. 1342–1346 which describes work done at the Naval Research Laboratories in Washington, D.C.; Naval Research Laboratory Report 111437, dated Apr. 15, 1954; U.S. Pat. Nos. 3,715,251; 3,704,198; 3,676,242; and 3,595,245; and British Specification No. 1,217,892.

A third layer of nonwoven fabric comprising multicomponent polymeric strands, as in the first web, can be bonded to the side of the second web opposite from the first web. When the second web is a meltblown layer, the meltblown layer is sandwiched between two layers of multicomponent material. Such material 50 is illustrated in FIGS. 3 and 4 and is advantageous as a medical garment material because it contains a liquid penetration resistant middle layer 52 with relatively soft layers of fabric 54 and 56 on each side for better softness and feel. The material 50 is preferably thermal point bonded. When thermal point bonded, the individual layers 52, 54, and 56 are fused together at bond points 58.

Such composite materials may be formed separately and then bonded together or may be formed in a continuous process wherein one web is formed on top of the other. Both of such processes are well known to those skilled in the art and are not discussed here in further detail. U.S. Pat. No. 4,041,203, which is incorporated herein by reference above, discloses both a continuous process and the use of preferred webs for making such composite materials.

Figure 5:
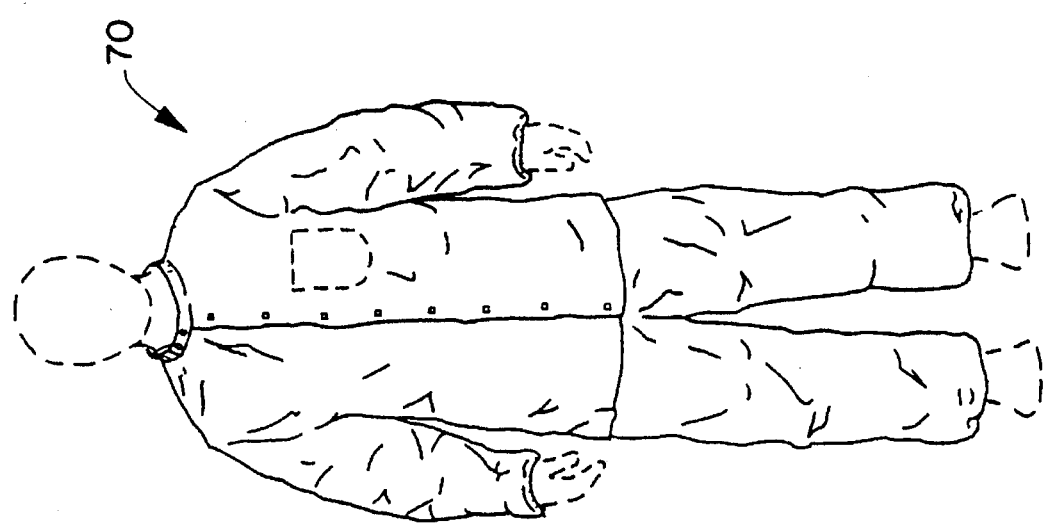
FIG. 5 is a perspective view of a medical garment made with nonwoven fabric according to a preferred embodiment of the present invention.

A medical garment 70 made according to an embodiment of the present invention is shown in FIG. 5. The construction of such garments of nonwoven fabric is well-known to those skilled the art and thus is not discussed here in detail. For example, process for making medical garments is disclosed in U.S. Pat. No. 4,523,336, the disclosure of which is expressly incorporated herein by reference.

Figure 6:
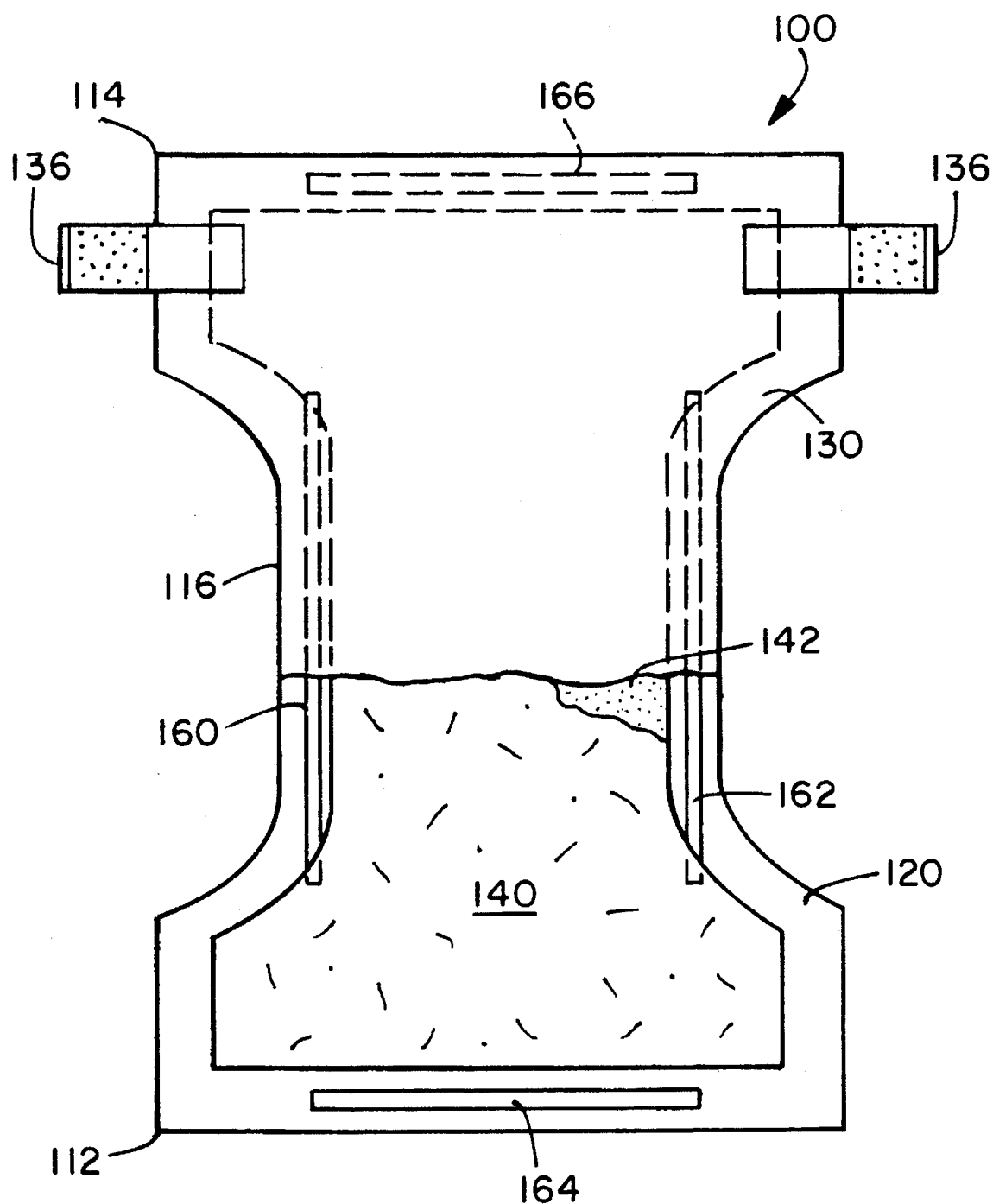
FIG. 6 is a partial plan view of an absorbent diaper type article made according to a preferred embodiment of the present invention. Portions of some layers of the articles have been removed to expose the interior of the article.

Turning to FIG. 6, a disposable diaper-type article 100 made according to a preferred embodiment of the present invention is shown. The diaper 100 includes a front waistband panel section 112, a rear waistband panel section 114, and an intermediate section 116 which interconnects the front and rear waistband sections. The diaper comprises a substantially liquid impermeable outer cover layer 120, a liquid permeable liner layer 130, and an absorbent body 140 located between the outer cover layer and the liner layer. Fastening means, such as adhesive tapes 136 are employed to secure the diaper 100 on a wearer. The liner 130 and outer cover 120 are bonded to each other and to absorbent body 140 with lines and patterns of adhesive, such as a hot-melt, pressure-sensitive adhesive. Elastic members 160, 162, 164 and 166 can be configured about the edges of the diaper for a close fit about the wearer.

The outer cover layer 120 can be composed of the fabric of the present invention bonded to a polymer film comprising polyethylene, polypropylene or the like.

The liner layer 130 and absorbent body 140 can also be made of the nonwoven fabric of the present invention. It is desirable that both the liner layer 130 and the absorbent body 140 be hydrophilic to absorb and retain aqueous fluids such as urine. Although not shown in FIG. 6, the disposable diaper 100 may include additional fluid handling layers such as a surge layer, a transfer layer or a distribution layer. These layers may be separate layers or may be integral with the liner layer 120 or the absorbent pad 14.

Although the absorbent article 100 shown in FIG. 6 is a disposable diaper, it should be understood that the nonwoven fabric of the present invention may be used to make a variety of absorbent articles such as those identified above.

Figure 7:
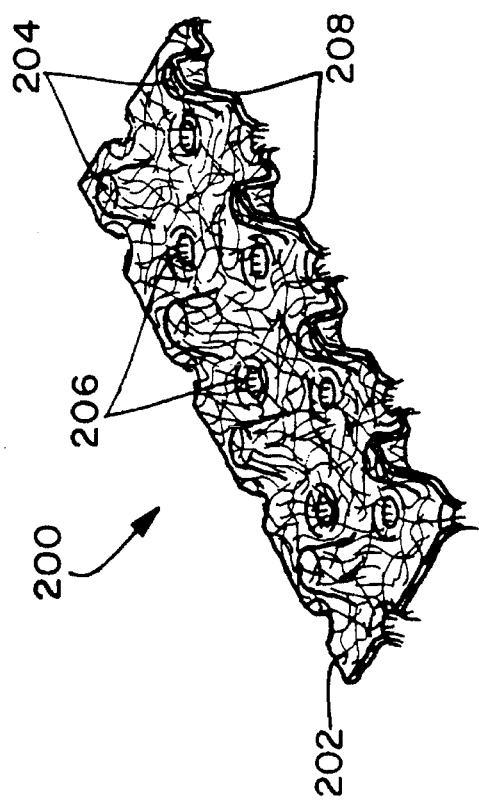
FIG. 7 is a partial perspective view of a shaped nonwoven fabric made according to a preferred embodiment of the present invention.

According to yet another embodiment of the present invention, the filaments from the fiber draw unit 22 can be formed on a textured forming surface so that the resulting nonwoven web assumes the textured pattern of the forming surface. The strands of the present invention are very soft and conformable when exiting the fiber draw unit 22, but become set quickly on the forming surface and take the shape of the forming surface. The resulting material becomes very resilient without becoming stiff or hard. Suitable textured forming surfaces are shown in U.S. Pat. No. 4,741,941, the disclosure of which is expressly incorporated herein by reference. A textured nonwoven web 200 made according to an embodiment of the present invention is shown in FIG. 7. The web 200 has a surface 202 with projected portions 204 extending from the surface and an array of apertures 206 separated by land areas 208.

The following Examples 1–6 are designed to illustrate particular embodiments of the present invention and to teach one of ordinary skill in the art in the manner of carrying out the present invention. Comparative Examples 1–3 are designed to illustrate the advantages of the present invention. All of the examples illustrate actual products that were made, except for Example 6 which is a prophetic example. It should be understood by those skilled in the art that the parameters of the present invention will vary somewhat from those provided in the following Examples depending on the particular processing equipment that is used and the ambient conditions.

COMPARATIVE EXAMPLE 1

A nonwoven fabric web comprising continuous bicomponent filaments was made with the process illustrated in FIG. 1 and described above. The configuration of the filaments was concentric sheath/core, the weight ratio of sheath to core being 1:1. The spinhole geometry was 0.6 mm D with an L/D ratio of 4:1 and the spinneret had 525 openings arranged with 50 openings per inch in the machine direction.

The core composition was 100% by weight PD-3495 polypropylene from Exxon Chemical Company of Houston, Tex., and the sheath composition was 100% by weight 9355 random copolymer of ethylene and propylene from Exxon. The random copolymer comprised 3% by weight ethylene. The melt temperature in the spin pack was 430° F. and the spinhole throughput was 0.7 GHM. The quench air flow rate was 22 scfm and the quench air temperature was 55° F. The aspirator feed temperature was 55° F. and the manifold pressure was 5 psi. The resulting nonwoven web was thermal point bonded at a bond temperature of 280° F. The bond pattern had regularly spaced bond areas with 270 bond points per square inch and a total bond area of about 18%. The filaments had a denier of 3.

EXAMPLE 1

A nonwoven fabric web comprising continuous bicomponent filaments was made with the process illustrated in FIG. 1 and described above. The configuration of the filaments was concentric sheath/core, the weight ratio of sheath to core being 1:1. The spinhole geometry was 0.6 mm D with an L/D ratio of 4:1 and the spinneret had 525 openings arranged with 50 openings per inch in the machine direction. The core composition was 100% by weight 3495 polypropylene from Exxon Chemical Company of Houston, Tex., and the sheath composition was 90% by weight 9355 random copolymer of ethylene and propylene (3% ethylene) from Exxon and 10% by weight KS-057P heterophasic polypropylene composition from Himont Incorporated of New Castle County, Del. The melt temperature in the spin pack was 430° F. and the spinhole throughput was 0.7 GHM. The quench air flow rate was 22 scfm and the quench air temperature was 55° F. The aspirator feed temperature was 55° F. and the manifold pressure was 5 psi. The resulting nonwoven web was thermal point bonded at a bond temperature of 275° F. The bond pattern had regularly spaced bond areas with 270 bond points per square inch and a total bond area of about 18%. The strands had a denier of 3.

EXAMPLE 2

A nonwoven fabric was made according to the process described in Example 1 except that the sheath component was 80% by weight 9355 random copolymer of ethylene and propylene from Exxon and 20% by weight of KS-057P heterophasic polypropylene composition.

EXAMPLE 3

A nonwoven fabric was made according to the process described in Example 1 except that the sheath component was 70% by weight 9355 random copolymer of ethylene and propylene from Dow and 30% by weight of KS-057P heterophasic polypropylene composition.

Fabric samples from Comparative Example 1 and Examples 1–3 were tested to determine their physical properties. The data from these tests are shown in Tables 1 and 2. The numbers not enclosed by parentheses or brackets represent actual data, the numbers in parentheses represent normalized data, and the numbers in brackets represent the percentage increase or decrease of the actual data relative to the data from the comparative example.

The grab tensile (peak energy, peak load, and peak elongation) was measured according to ASTM D 1682.

The trapezoid tear is a measurement of the tearing strength of fabrics when a constantly increasing load is applied parallel to the length of the specimen. The trapezoid tear was measured according to ASTM D 1117-14 except that the tearing load was calculated as the average of the first and highest peaks recorded rather than of the lowest and highest peaks.

The abrasion resistance was measured according to two tests, the first being the Martindale Abrasion test which measures the resistance to the formation of pills and other related surface changes on textile fabrics under light pressure using a Martindale tester. The Martindale Abrasion was measured according to ASTM 04970-89 except that the value obtained was the number of cycles required by the Martindale tester to create a 0.5 inch hole in the fabric sample.

The second abrasion resistance test was the double head rotary platform (Tabor) test. The Tabor test was performed according to ASTM D-1175 using a 125 gram rubber wheel. The abrasion resistance was measured in cycles to a 0.5 inch hole.

The drape stiffness was measured according to ASTM D 1388.

TABLE 1

|  | COMPARATIVE EXAMPLE 1 | EXAMPLE 1 | EXAMPLE 2 | EXAMPLE 3 |
| --- | --- | --- | --- | --- |
| Basis Weight (ounce/yd$^2$) | 1.07 (1.1) | 1.28 (1.1) | 1.1 (1.1) | 1.16 (1.1) |
| MD Peak Energy (in-lb) | 18.1 (18.6) | 33.6 (28.5) [153%] | 22.8 (22.8) [122%] | 22.8 (21.6) [116%] |
| MD Peak Load (lb) | 17.6 (18.1) | 26.4 (22.7) [125%] | 19.3 (19.3) [107%] | 17.6 (16.7) [92%] |
| MD Peak Elongation (%) | 55.4 (55.4) | 67.1 (67.1) [121%] | 64.3 (64.3) [116%] | 71.1 (71.1) [128%] |
| CD Peak Energy (in-lb) | 12.8 (13.1) | 26.6 (22.8) [174%] | 27.3 (27.3) [208%] | 17.1 (16.2) [124%] |
| CD Peak Load (lb) | 11.8 (12.1) | 19.3 (16.6) [137%] | 16.1 (16.1) [133%] | 13.1 (12.4) [102%] |
| CD Peak | 62.9 | 82 | 96.8 | 80.3 |

TABLE 1-continued

|  | COMPARATIVE EXAMPLE 1 | EXAMPLE 1 | EXAMPLE 2 | EXAMPLE 3 |
| --- | --- | --- | --- | --- |
| Elongation (in) | (62.9) | (82) [130%] | (96.8) [154%] | (80.3) [128%] |
| MD/CD Average | 15.4 (15.9) | 29.9 (25.7) [162%] | 25.1 (25.1) [158%] | 20.0 (18.9) [119%] |
| Peak Energy (in-lb) MD/CD Average Peak Load (lb) | 14.7 (15.1) | 22.8 (19.6) [130%] | 17.7 (17.7) [117%] | 15.3 (14.6) [96%] |
| Trap Tear (lb) MD | 7.25 | 11.27 [155%] | 8.29 [114%] | 8.66 [119%] |
| CD | 6.43 | 7.97 [124%] | 7.08 [110%] | 6.46 [100%] |

TABLE 2

|  | COMPARATIVE EXAMPLE 1 | EXAMPLE 1 | EXAMPLE 2 | EXAMPLE 3 |
| --- | --- | --- | --- | --- |
| Martindale Abrasion Cycles to 0.5 in hole | 616 | 1262 [205%] | 1518 [246%] | 1122 [182%] |
| Martindale Abrasion, Cycles to Rating Photo (1–5) | 5 | 5 [100%] | 5 [100%] | 5 [100%] |
| Taber Abrasion, 1-CS10 Wheel | 76 | 150 [197%] | 84 [110%] | 49 [64%] |
| Drape MD (in) | 2.73 | 3.90 [143%] | 2.86 [105%] | 2.68 [98%] |
| Drape MD (in) | 2.21 | 2.54 [115%] | 1.91 [86%] | 1.97 [89%] |

As can be seen from the data in Tables 1 and 2, the addition of the KS-057P heterophasic polypropylene composition substantially increased the strength properties of the fabric samples from Examples 1–3 over the sample fabric from Comparative Example 1. The lower loadings of KS-057P produced the stronger fabrics. The abrasion resistance test results were mixed, but the overall results indicate that abrasion resistance was improved, especially at lower loadings of KS057P. The Drape stiffness test results were also mixed, but indicate that the softness of the fabrics from Examples 1–3 was comparable to the softness of the fabric sample from Comparative Example 1. The softness was enhanced at higher loadings of KS-057P.

COMPARATIVE EXAMPLE 2

A nonwoven fabric web comprising continuous bicomponent filaments was made with the process illustrated in FIG. 1 and described above. The configuration of the filaments was concentric sheath/core, the weight ratio of sheath to core being 1:1. The spinhole geometry was 0.6 mm D with an L/D ratio of 4:1 and the spinneret had 525 openings arranged with 50 openings per inch in the machine direction. The core composition was 100% by weight PD-3495 polypropylene from Exxon Chemical Company of Houston, Tex., and the sheath composition was 100% by weight 9355 random copolymer of ethylene and propylene from Exxon. The random copolymer comprised 3% by weight ethylene. The melt temperature in the spin pack was 430° F. and the spinhole throughput was 0.7 GHM. The quench air flow rate was 22 scfm and the quench air temperature was 55° F. The aspirator feed temperature was 55° F. and the manifold pressure was 5 psi. The resulting nonwoven web was thermal point bonded at a bond temperature of 260° F. The bond pattern had regularly spaced bond areas with 270 bond points per square inch and a total bond area of about 18%. The filaments had a denier of 3.4.

EXAMPLE 4

A nonwoven fabric web comprising continuous bicomponent filaments was made with the process illustrated in FIG. 1 and described above. The configuration of the filaments was concentric sheath/core, the weight ratio of sheath to core being 1:1. The spinhole geometry was 0.6 mm D with an L/D ratio of 4:1 and the spinneret had 525 openings arranged with 50 openings per inch in the machine direction. The core composition was 100% by weight 3495 polypropylene from Exxon Chemical Company of Houston, Tex., and the sheath composition was 80% by weight 9355 random copolymer of ethylene and propylene (3% ethylene) from Exxon and 20% by weight KS-057P heterophasic polypropylene composition from Himont Incorporated of New Castle County, Del. The melt temperature in the spin pack was 430° F. and the spinhole throughput was 0.7 GHM. The quench air flow rate was 22 scfm and the quench air temperature was 55° F. The aspirator feed temperature was 55° F. and the manifold pressure was 5 psi. The resulting nonwoven web was thermal point bonded at a bond temperature of 260° F. The bond pattern had regularly spaced bond areas with 270 bond points per square inch and a total bond area of about 18%. The filaments had a denier of 3.4.

Fabric samples from Comparative Example 2 and Example 4 were tested to determine their physical properties using the same test methods used to test the samples of fabric from Examples 1–3 and an additional test method described below. The data from these tests are shown in Tables 3 and 4. Again, the numbers not enclosed by parentheses or brackets represent actual data, the numbers in parentheses represent normalized data, and the numbers in brackets represent the percentage increase or decrease of the actual data relative to the data from the comparative example.

The cup crush test evaluates fabric stiffness by measuring the peak load required for a 4.5 cm diameter hemispherically shaped foot to crush a 9"∓9" piece of fabric shaped into an approximately 6.5 cm diameter by 6.5 cm tall inverted cup while the cup shaped fabric is surrounded by an approximately 6.5 cm diameter cylinder to maintain a uniform deformation of the cup shaped fabric. The foot and the cup are aligned to avoid contact between the cup walls and the foot which might affect the peak load. The peak load is measured while the foot descends at a rate of about 0.25 inches per second (15 inches per minute) utilizing a Model FTD-G-500 load cell (500 gram range) available from the Schaevitz Company, Tennsauken, N.J.

TABLE 3

|  | EXAMPLE 2 | COMPARATIVE EXAMPLE 4 |
|---|---|---|
| Basis Weight (ounce/yd²) | 1.07 (1.1) | 1.14 (1.1) |
| MD Peak Energy (in-lb) | 22.3 (23.0) | 28.2 (27.2) [118%] |
| MD Peak Load (lb) | 21.0 (21.6) | 23.2 (22.4) [103%] |
| MD Peak Elongation % | 56.9 (56.8) | 71.1 (71.1) [125%] |
| CD Peak Energy (in-lb) | 13.3 (13.7) | 28.1 (27.2) [198%] |
| CD Peak Load (lb) | 12.3 (13.3) | 19.8 (19.1) [144%] |
| CD Peak Elongation (in) | 60.0 (60.0) | 85.0 (85.0) [142%] |
| MD/CD Average Peak Energy (in-lb) | 17.8 (18.3) | 28.2 (27.2) [149%] |
| MD/CD Average Peak Load (lb) | 16.9 (17.4) | 21.5 (20.7) [119%] |
| Trap Tear (lb) MD | 10.9 | 13.3 [122%] |
| CD | 4.0 | 9.0 [225%] |

TABLE 4

|  | EXAMPLE 2 | COMPARATIVE EXAMPLE 4 |
|---|---|---|
| Martindale Abrasion Cycles to 0.5 in hole | 734 | 699 [95.2%] |
| Martindale Abrasion, Cycles to Rating Photo (1–5) | 5 | 5 [100%] |
| Taber Abrasion, 1-CS10 Wheel | 80 | 182 [227%] |
| Drape MD (in) | 3.46 | 2.96 [85.5%] |
| Drape CD (in) | 2.54 | 2.41 [94.8%] |
| Cup Crush Peak Load (g) | 114 | 123 [108%] |
| Cup Crush Total Energy (g/mm) | 2030 | 2311 [114%] |

The addition of KS-057P to the composite fabric in Example 4 produced results very similar to those shown in Tables 1 and 2 for Examples 1–3. The strength was increased significantly and the abrasion resistance and softness were at least comparable. The abrasion resistance test results were mixed, the Martindale abrasion showing a decrease in abrasion resistance and the Tabor abrasion showing a increase in abrasion resistance. The softness test results were also mixed with the drape test showing a softer fabric and the cup crush showing a stiffer fabric.

COMPARATIVE EXAMPLE 3

A nonwoven fabric web comprising continuous bicomponent filaments was made with the process illustrated in FIG. 1 and described above. The configuration of the filaments was concentric sheath/core, the weight ratio of sheath to core being 1:1. The spillhole geometry was 0.6 mm D with an L/D ratio of 4:1 and the spinneret had 525 openings arranged with 50 openings per inch in the machine direction. The core composition was 100% by weight PD-3495 polypropylene from Exxon Chemical Company of Houston, Tex., and the sheath composition was 100% by weight 9355 random copolymer of ethylene and propylene from Exxon. The random copolymer comprised 3% by weight ethylene. The melt temperature in the spin pack was 430° F. and the spinhole throughput was 0.7 GHM. The quench air flow rate was 22 scfm and the quench air temperature was 55° F. The aspirator feed temperature was 55° F. and the manifold pressure was 7 psi. The resulting nonwoven web was thermal point bonded at a bond temperature of 280° F. The bond pattern had regularly spaced bond areas with 270 bond points per square inch and a total bond area of about 18%. The filaments had a denier of 2.1.

EXAMPLE 5

A nonwoven fabric web comprising continuous bicomponent filaments was made with the process illustrated in FIG. 1 and described above. The configuration of the filaments was concentric sheath/core, the weight ratio of sheath to core being 1:1. The spinhole geometry was 0.6 mm D with an L/D ratio of 4:1 and the spinneret had 525 openings arranged with 50 openings per inch in the machine direction. The core composition was 100% by weight 3495 polypropylene from Exxon Chemical Company of Houston, Tex., and the sheath composition was 80% by weight 9355 random copolymer of ethylene and propylene (3% ethylene) from Exxon and 20% by weight KS-057P heterophasic polypropylene composition from Himont Incorporated of New Castle County, Del. The melt temperature in the spin pack was 430° F. and the spinhole throughput was 0.7 GHM. The quench air flow rate was 22 scfm and the quench air temperature was 55° F. The aspirator feed temperature was 55° F. and the manifold pressure was 7 psi. The resulting nonwoven web was thermal point bonded at a bond temperature of 280° F. The bond pattern had regularly spaced bond areas with 270 bond points per square inch and a total bond area of about 18%. The filaments had a denier of 2.1.

Fabric samples from Comparative Example 3 and Example 5 were tested to determine their physical properties using the same test methods used to test the samples of fabric from Examples 1–4 and an additional test method described below. The data from these tests are shown in Tables 5 and 6. Again, the numbers not enclosed by parentheses or brackets represent actual data, the numbers in parentheses represent normalized data, and the numbers in brackets represent the percentage increase or decrease of the actual data relative to the data from the comparative example.

For Comparative Example 3 and Example 5, the softness of the fabric samples was also tested using the Cusick drape method.

The Cusick drape test was performed with the Rotrakote-Cusick drape tester available from Rotrakote Converting Limited, New York, N.Y. First, a sheet of drawing paper is placed flat on the base of the tester with the pin in the base projecting through the paper. A weight is placed on one corner of the paper. The support disc is placed in its lower position and a 36 cm diameter, circular piece of fabric is placed flat on the platform with the pin in the support disc through the center of the sample. The sample is oriented with the machine direction running front to back and the disc cover is placed on the support disc. The support disc is raised to its upper position and locked at that position. The exact outline of the shadow cast by the sample is then marked on the drawing paper. The drawing paper is removed from the tester and the area within the shadow outline is measured using a K&E Planimeter Model Number 620015

The area of the shadow cast by the sample is measured by placing the pole weight of the planimeter over the center hole in the drawing with the pole arm pointing toward the operator, the tracer arm pointing to the right, and the tracer at the starting point. The wheel and dial scales are set to zero. The shadow outline is then traced in a clockwise direction until the tracer returns to the starting point. The scales are then read, the dial numbers being 1000 vernier units each, the wheel numbers 100 verniers each, and the small divisions on the wheel 10 each. If the dial makes less than 1 revolution per trace then the draped area in square inches equals (vernier units)/100+100. If the dial makes more than 1 revolution per trace then the draped area in square inches equals (vernier units)/100. The drape coefficient then equals $100 \mp$ (area of draped sample—area of support disc)/(area of template—area of support disc).

TABLE 5

|  | EXAMPLE 3 | COMPARATIVE EXAMPLE 5 | EXAMPLE 4 | COMPARATIVE EXAMPLE 6 |
| --- | --- | --- | --- | --- |
| Basis Weight (ounce/yd$^2$) | 1.00 | 1.02 | 1.54 (1.50) | 1.48 (1.50) |
| MD Peak Energy (in-lb) | 26.3 | 26.9 [102%] | 14.4 (14.0) | 21.2 (21.5) [153%] |
| MD Peak Load (lb) | 20.1 | 17.6 [88%] | 17.8 (17.3) | 18.8 (19.0) [110%] |
| MD Peak Elongation (%) | 75.9 | 88.1 [116%] | 39.7 (39.7) | 56.0 (56.0) [141%] |
| CD Peak Energy (in-lb) | 20.7 | 27.5 [133%] | 15.0 (14.5) | 18.1 (18.3) [126%] |
| CD Peak Load (lb) | 14.2 | 14.2 [100%] | 12.2 (11.9) | 13.0 (13.1) [110%] |
| CD Peak Elongation (in) | 92 | 117.4 [128%] | 67.9 (67.9) | 80.6 (80.6) [139%] |
| MD/CD Average Peak Energy (in-lb) | 23.5 | 27.2 [115%] | 14.7 (14.3) | 19.6 (19.9) [139%] |
| MD/CD Average Peak Load (lb) | 17.1 | 15.9 [92%] | 15.0 (14.6) | 15.9 (16.1) [110%] |
| Trap Tear (lb) MD | 9.6 | 9.5 [99%] | 7.13 | 8.86 [124%] |
| CD | 6.7 | 6.1 [91%] | 4.13 | 6.92 [168%] |

TABLE 6

|  | EXAMPLE 3 | COMPARATIVE EXAMPLE 5 | EXAMPLE 4 | COMPARATIVE EXAMPLE 6 |
| --- | --- | --- | --- | --- |
| Martindale | 616 | 3654 | 1213 | 2089 |

TABLE 6-continued

|  | EXAMPLE 3 | COMPARATIVE EXAMPLE 5 | EXAMPLE 4 | COMPARATIVE EXAMPLE 6 |
| --- | --- | --- | --- | --- |
| Abrasion Cycles to 0.5 in hole | | [593%] | | [172%] |
| Martindale Abrasion, Cycles to Rating Photo (1–5) | 3 | 4 [133%] | 4.8 | 5 [105%] |
| Taber Abrasion, 1-CS10 Wheel | — | — | 59 | 46 [78%] |
| Drape MD (in) | 3.35 | 3.59 [107%] | 3.57 | 4.16 [116%] |
| Drape CD (in) | 2.4 | 2.72 [113%] | 2.52 | 2.56 [102%] |
| Cup Crush Peak Load (g) | 79 | 68 [86%] | 233 | 193 [83%] |
| Cup Crush Total Energy (g/mm) | 1448 | 1324 [91%] | 4229 | 3726 [88%] |
| Cusick Drape (%) | 51.2 | 48.9 [96%] | — | — |

As can be seen from the data in Tables 5 and 6, the addition of KS-057P in Example 5 significantly increased the abrasion resistance of the fabric as compared to the fabric sample of Comparative Example 3; however, the results of the strength and softness tests were mixed. The peak elongation and peak energy were increased, but the peak load was decreased. Meanwhile, the drape stiffness indicated a slight stiffening of the fabric, but the cup crush and cusick drape indicated a slight softening. The KS-057P used in Example 5 came from a different gaylord than the KS-057P used in Examples 1–3 and it is believed that the gaylord of KS-057P used in Example 5 was atypical. Nevertheless, the addition of the KS-057P in Example 5 still enhanced the overall properties of the fabric. The durability of the fabric was increased while the strength and softness remained comparable to the comparative sample.

COMPARATIVE EXAMPLE 4

A first nonwoven fabric web comprising continuous bicomponent filaments was made with the process illustrated in FIG. 1 and described above. The configuration of the filaments was concentric sheath/core, the weight ratio of sheath to core being 1:1. The spinhole geometry was 0.6 mm D with an L/D ratio of 4:1 and the spinneret had 525 openings arranged with 50 openings per inch in the machine direction. The core composition was 100% by weight PD-3495 polypropylene from Exxon Chemical Company of Houston, Tex., and the sheath composition was 100% by weight 9355 random copolymer of ethylene and propylene from Exxon. The melt temperature in the spin pack was 430° F. and the spinhole throughput was 0.7 GHM. The quench air flow rate was 22 scfm and the quench air temperature was 55° F. The aspirator feed temperature was 55° F. and the manifold pressure was 7 psi. The web was thermal point bonded to opposite sides of a middle meltblown nonwoven fabric web comprising 100% by weight 3495G polypropylene available from Exxon. The composite was made in accordance with U.S. Pat. No. 4,041,203. The resulting composite was thermal point bonded at a bond temperature of 280° F. The bond pattern had regularly spaced bond areas with 270 bond points per square inch and a total bond area of about 18%.

EXAMPLE 6

A first nonwoven fabric web comprising continuous bicomponent filaments was made with the process illustrated in FIG. 1 and described above. The configuration of the filaments was concentric sheath/core, the weight ratio of sheath to core being 1:1. The spinhole geometry was 0.6 mm D with an L/D ratio of 4:1 and the spinneret had 525 openings arranged with 50 openings per inch in the machine direction. The core composition was 100% by weight 3495 polypropylene from Exxon Chemical Company of Houston, Tex., and the sheath composition was 70% by weight 9355 random copolymer of ethylene and propylene from Exxon and 30% by weight KS-057P heterophasic polypropylene composition available from Himont Inc.. The melt temperature in the spin pack was 430° F. and the spinhole throughput was 0.7 GHM. The quench air flow rate was 22 scfm and the quench air temperature was 55° F. The aspirator feed temperature was 55° F. and the manifold pressure was 7 psi. The first web was thermal point bonded to opposite sides of a middle meltblown nonwoven fabric web comprising 100% by weight 3495G polypropylene available from Exxon. The composite was made in accordance with U.S. Pat. No. 4,041,203. The resulting composite was thermal point bonded at a bond temperature of 275° F. The bond pattern had regularly spaced bond areas with 270 bond points per square inch and a total bond area of about 18%.

Fabric samples from Comparative Example 4 and Example 6 were tested to determine their physical properties using the same test methods used to test the samples of fabric from the foregoing examples. The data from these tests are shown in Tables 5 and 6. Again, the numbers not enclosed by parentheses or brackets represent actual data, the numbers in parentheses represent normalized data, and the numbers in brackets represent the percentage increase or decrease of the actual data relative to the data from the comparative example.

The addition of KS-057P to the composite fabric in Example 6 produced results very similar to those shown in Tables 1 and 2 for Examples 1–3. The strength was increased significantly and the abrasion resistance and softness were at least comparable if not enhanced. The abrasion resistance test results were mixed, the Martindale abrasion showing an increase in abrasion resistance and the Tabor abrasion showing a decrease in abrasion resistance. The softness test results were also mixed with the drape test showing a stiffer fabric and the cup crush showing a softer fabric.

EXAMPLE 7

This Example was not actually carried out, but is included to demonstrate to those skilled in the art the manner of making an embodiment of the present invention with single component filaments instead of bicomponent filaments. Here, a nonwoven fabric web comprising continuous bicomponent filaments is made with the process illustrated in FIG. 1 and described above except that the spinneret is designed for forming single component filaments. The spinhole geometry is 0.6 mm D with an L/D ratio of 4:1 and the spinneret has 525 openings arranged with 50 openings per inch in the machine direction. The filament composition is 90% by weight 9355 random copolymer of ethylene and propylene (3% ethylene) from Exxon Chemical Company of Houston, Tex. and 10% by weight KS057P heterophasic polypropylene composition from Himont Incorporated of New Castle County, Del. The melt temperature in the spin pack is 430° F. and the spinhole throughput is 0.7 GHM. The quench air flow rate is 22 scfm and the quench air temperature was 55° F. The aspirator feed temperature was 55° F. and the manifold pressure is 5 psi. The resulting nonwoven web is thermal point bonded at a bond temperature of 280° F. The bond pattern has regularly spaced bond areas with 270 bond points per square inch and a total bond area of about 18%. The strands have a denier of 3.

While the invention has been described in detail with respect to specific embodiments thereof, it will be appreciated that those skilled in the art, upon attaining an understanding of the foregoing, may readily conceive of alterations to, variations of and equivalents to these embodiments. Accordingly, the scope of the present invention should be assessed as that of the appended claims and any equivalents thereto.

We claim:

1. A nonwoven fabric comprising polymeric strands, said polymeric strands comprising a first polymeric component which comprises a blend of:
   (a) a melt-extrudable polyolefin, and
   (b) a polypropylene composition comprising:
      (i) a first polymer which is a propylene polymer comprising greater than 85% by weight of propylene and having an isotactic index greater than 85;
      (ii) a second polymer which is a polymer comprising ethylene and being insoluble in xylene at about 23° C.; and
      (iii) a third polymer which is an amorphous copolymer of ethylene and propylene, the amorphous copolymer being soluble in xylene at about 23° C.

2. A nonwoven fabric as in claim 1 wherein the polypropylene composition is present in the first polymeric component in an amount up to about 40% by weight.

3. A nonwoven fabric as in claim 1 wherein the first polymer is present in the polypropylene composition in an amount from about 10 to about 60 parts by weight, the second polymer is present in the polypropylene composition in an amount from about 10 to about 40 parts by weight, and the third polymer is present in the polypropylene composition in an amount from about 30 to about 60 parts by weight.

4. A nonwoven fabric as in claim 1 wherein the third polymer comprises ethylene in an amount from about 40 to about 70% by weight.

5. A nonwoven fabric as in claim 1 wherein the melt-extrudable polyolefin of the first polymeric component is selected from the group consisting of polypropylene, random copolymers of propylene and ethylene, and poly(4-methyl-1-pentene).

6. A nonwoven fabric as in claim 1 wherein the strands are multicomponent strands and further include a second melt-extrudable polymeric component, the strands having a cross-section, a length, and a peripheral surface, the first and second components being arranged in substantially distinct zones across the cross-section of the strands and extending continuously along the length of the strands, the first component constituting at least a portion of the peripheral surface of the strands continuously along the length of the strands.

7. A nonwoven fabric as in claim 6 wherein the polypropylene composition is present in the first polymeric component in an amount: up to about 40% by weight.

8. A nonwoven fabric as in claim 6 wherein the first polymer is present in the polypropylene composition in an amount from about 10 to about 60 parts by weight, the second polymer is present in the polypropylene composition in an amount from about 10 to about 40 parts by weight, and the third polymer is present in the polypropylene composition in an amount from about 30 to about 60 parts by weight.

9. A nonwoven fabric as in claim 6 wherein the third polymer comprises ethylene in an amount from about 40 to about 70% by weight.

10. A nonwoven fabric as in claim 6 wherein the melt-extrudable polyolefin of the first component is selected from the group consisting of polypropylene, random copolymers of propylene and ethylene, and poly(4-methyl-1-pentene).

11. A nonwoven fabric as in claim 6 wherein the second component comprises a crystalline polyolefin.

12. A nonwoven fabric as in claim 6 wherein the second component comprises a polyolefin selected from the group consisting of polypropylene, random copolymers of propylene and ethylene, and poly(4-methyl-1-pentene).

13. A nonwoven fabric as in claim 6 wherein the first and second components are arranged in a side-by-side configuration.

14. A nonwoven fabric as in claim 6 wherein the first and second components are arranged in a sheath/core configuration.

15. A nonwoven fabric as in claim 6 wherein the nonwoven fabric has a surface and projected portions extending from the surface.

16. A nonwoven fabric as in claim 6 wherein the nonwoven fabric has an array of apertures separated by land areas.

* * * * *